United States Patent
Dougherty et al.

(10) Patent No.: US 8,313,734 B2
(45) Date of Patent: Nov. 20, 2012

(54) MALODOUR COUNTERACTING COMPOSITION

(75) Inventors: Kenneth Paul Dougherty, Bethlehem, PA (US); Jana Pika, Princeton, NJ (US); Qiaoling Charlene Zeng, Eau Claire, WI (US)

(73) Assignee: Firmenich SA, Geneva (CH)

(*) Notice: Subject to any disclaimer, the term of this patent is extended or adjusted under 35 U.S.C. 154(b) by 412 days.

(21) Appl. No.: 12/517,188

(22) PCT Filed: Dec. 7, 2007

(86) PCT No.: PCT/IB2007/054963
§ 371 (c)(1),
(2), (4) Date: Jun. 1, 2009

(87) PCT Pub. No.: WO2008/078212
PCT Pub. Date: Jul. 3, 2008

(65) Prior Publication Data
US 2010/0055051 A1 Mar. 4, 2010

Related U.S. Application Data

(60) Provisional application No. 60/871,259, filed on Dec. 21, 2006.

(51) Int. Cl.
*A61K 8/00* (2006.01)
*A61K 31/05* (2006.01)
*A61L 9/01* (2006.01)

(52) U.S. Cl. ........... 424/49; 424/48; 424/76.4; 514/731; 514/734; 514/736

(58) Field of Classification Search .................. None
See application file for complete search history.

(56) References Cited

U.S. PATENT DOCUMENTS

| | | | | |
|---|---|---|---|---|
| 4,610,890 | A | 9/1986 | Miller et al. | 426/651 |
| 4,707,367 | A | 11/1987 | Miller et al. | 426/96 |
| 5,906,811 | A * | 5/1999 | Hersh | 424/54 |
| 6,080,391 | A * | 6/2000 | Tsuchiya et al. | 424/65 |
| 6,228,402 | B1* | 5/2001 | Wolf et al. | 426/94 |
| 6,287,542 | B1 | 9/2001 | Bernard et al. | 424/49 |
| 2002/0009436 | A1* | 1/2002 | Doyle et al. | 424/94.6 |
| 2002/0012633 | A1* | 1/2002 | Gmunder et al. | 424/48 |
| 2003/0026874 | A1* | 2/2003 | Porzio et al. | 426/96 |
| 2003/0049303 | A1* | 3/2003 | Ning et al. | 424/439 |
| 2004/0028622 | A1* | 2/2004 | Gurin | 424/48 |
| 2004/0037792 | A1* | 2/2004 | Hiramoto et al. | 424/65 |

FOREIGN PATENT DOCUMENTS

| | | |
|---|---|---|
| EP | 1 013 261 | 6/2000 |
| EP | 1 195 099 | 4/2002 |
| WO | WO 00/25606 | 5/2000 |
| WO | WO 01/17372 | 3/2001 |
| WO | WO 01/17494 | 3/2001 |
| WO | WO 0117494 A1 * | 3/2001 |
| WO | WO 01/85101 | 11/2001 |
| WO | WO 2004/014348 | 2/2004 |
| WO | WO 2005092112 A1 * | 10/2005 |

OTHER PUBLICATIONS

AK Williams, JT Hupp. "Sol-Gel-Encapsulated Alcohol Dehydrogenase as a Versatile, Environmentally Stabilized Sensor for Alcohols and Aldehydes." Journal of the American Chemical Society, vol. 120, 1998, pp. 4366-4371.*
O Negishi, T Ozawa. "Effect of Polyphenol Oxidase on Deodorization." Biosci. Biotech. Biochem., vol. 61 Issue 12, 1997, pp. 2080-2084.*
International Search Report, PCT/IB2007/054963, dated May 16, 2008.
Osamu, Negishi et al., "Effects of Food Materials on Removal of Allium-Specific Volatile Sulfur Compounds", Journal of Agricultural and Food Chemistry, vol. 50, pp. 3856-3861, 2002.
Sakanaka, S., "Green Tea Polyphenols for Prevention of Dental Caries", CRC Press LLC, pp. 87-101, 1997.
Nagle, Dale G. et al., "Epigallocatechin-3-gallate (EGCG): Chemical and Biomedical Perspectives", Elsevier Ltd., Science Direct, Phytochemistry, vol. 67, pp. 1849-1855, 2006.

* cited by examiner

*Primary Examiner* — Frederick Krass
*Assistant Examiner* — Isaac Shomer
(74) *Attorney, Agent, or Firm* — Winston & Strawn LLP

(57) ABSTRACT

A composition for counteracting malodour due to thiols, with the composition including a polyphenol, a source of polyphenol, a composition comprising polyphenol or mixtures thereof, a base, and optionally, an enzyme, wherein the polyphenol is encapsulated. The polyhenol is preferably a green tea extract and the enzyme is polyphenol (per)oxidase acetone powder.

16 Claims, No Drawings

MALODOUR COUNTERACTING COMPOSITION

This application is a 371 filing of International Patent Application PCT/IB2007/054963 filed Dec. 7, 2007, which claims the benefit of application No. 60/871,259 filed Dec. 21, 2006.

TECHNICAL FIELD

The present invention relates to a malodour counteracting composition and more preferably to an oral care product comprising a malodour counteracting composition.

BACKGROUND AND PRIOR ART

It is well known that a considerable problem of oral hygiene is offensive breath, also called bad breath, foetor ex oris or halitosis. Since social contacts are often impeded by bad breath, those affected have a great interest in remedying or preventing it.

Bad breath is primarily due to volatile sulphur-containing compounds which are generated when bacteria feed off residues of food and dead cells within the oral cavity. The principal sulphur-containing compounds which are responsible are thiols, particularly methanethiol, as well as hydrogen sulphide.

Numerous compositions for combating bad breath have been described in the art. For instance, it is well known to use chlorhexidine to fight against the bacteria responsible for bad breath, however this can result in dental discoloration. It is also common practice to provide minty flavoured chewing gums, breathmints or edible films to mask the malodour but these do little or nothing to reduce or eliminate it.

Thus, it would be desirable to provide a composition which reduces the presence of the unwanted thiols.

WO-A1-2004/014348 (Michael Gurin) discloses compositions comprising polyphenol and enzymes which can be used to control halitosis. The polyphenol is mixed with citric acid to prevent ionization of the hydroxyl groups on the polyphenol. Furthermore, the enzyme is typically encapsulated together with the polyphenol. In addition, the purpose is to destroy the bacteria present in the mouth rather than to address the presence of thiols.

It would also be desirable to provide a composition in which any of the active ingredients are stable upon storage and yet, when mixed, provide a synergistic effect to control malodour due to thiols.

Furthermore, it would be desirable to provide a composition that maintains an excellent effect against malodour even in a pH environment at which the active ingredients may typically be unstable during storage.

Thus, the present invention seeks to address one or more of the abovementioned problems and/or to provide one or more of the abovementioned benefits.

SUMMARY OF THE INVENTION

The present invention provides a composition for counteracting malodour due to thiols, the composition comprising:
(i) a polyphenol, a source of polyphenol, a composition comprising polyphenol or mixtures thereof,
(ii) a base, and optionally
(iii) an enzyme,
wherein component (i) is encapsulated.

In another aspect there is provided an oral care product comprising the composition of the invention.

In still another aspect there is provided chewing gum comprising the composition of the invention.

In yet another aspect there is provided a toothpaste comprising the composition of the invention.

In still yet another aspect there is provided a mouth rinse powder premix comprising the composition of the invention.

According to a further aspect, there is provided the use of a composition of the invention to reduce malodour due to thiols.

In yet a further aspect, there is provided a method of preparing a composition for reducing malodour due to thiols comprising the steps of
(i) encapsulating a polyphenol or polyphenol-containing material,
(ii) mixing the encapsulated polyphenol or polyphenol-containing material with a base and optionally an enzyme.

DETAILED DESCRIPTION OF THE INVENTION

Polyphenol

The composition of the invention comprises, as component (i), a polyphenol, a source of polyphenol, a composition comprising a polyphenol or mixtures thereof.

Preferably the polyphenol is substituted with a ring comprising at least two hydroxyl groups in the meta or para position. It is believed that these hydroxyl groups can oxidise and then undergo a reaction with a thiol thereby eliminating or, at least, reducing the malodour due to thiols.

It is particularly preferred that the polyphenol has the formula:

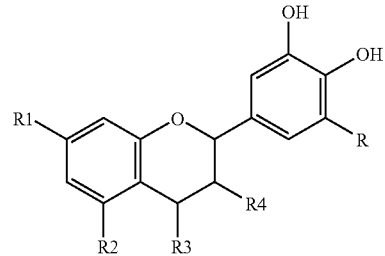

wherein
R, R1 and R2 are independently selected from H or —OH,
R3 is H, —OH or =O, and
R4 is —OH or

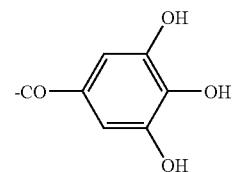

Polyphenols of this formula are found to provide particularly effective control of malodour due to the presence of thiols.

In this class of compounds, it is has been found that a number of suitable polyphenols are to be found as naturally occurring ingredients in tea.

Tea is obtained from the *Camellia sinensis* plant. It is present in many forms, including leaf, stem, xylem, root, nut or mixtures thereof, though it is most commonly present as tea leaves for drinking.

The tea leaf for drinking includes fermented tea such as black tea and puahru tea, half-fermented tea such as oolong tea and paochoncha, non-fermented tea such as green tea, kamairi (infused in a pot) green tea and houjicha, and mixtures thereof. The tea ingredients, suitable for use in the present invention, can be used from any of the above-mentioned sources, though green tea and/or fermented are more preferred, and green tea is especially preferred.

As component (i), the tea-derived polyphenols may be provided as the tea itself Alternatively, it may be provided as an extract typically obtained by extraction using, for instance, water, organic solvent, water-containing organic solvent, or a mixture thereof.

Thus component (i) may advantageously be a source of polyphenol, more preferably a natural extract, even more preferably a tea extract, most preferably a green tea extract.

If component (i) is provided as an extract, it may be further refined. Refinement can be carried out by any suitable manner, many of which are known to the person skilled in the art.

A tea-derived polyphenol for use as component (i) may be selected from (+)-catechin, (−)-catechin, (+)-gallocatechin, (+)-epigallocatechin, (+)-gallocatechin gallate, (+)-epigallocatechin gallate, (−)-epicatechin, (−)-epicatechin gallate, (−)-catechin gallate, (−)-epigallocatechin, (−)-gallocatechin, (−)-epigallocatechin gallate, (−)-gallocatechin gallate, theaflavin monogallate A, theaflavin monogallate B, theaflavin digallate, and free theaflavin.

A particularly preferred polyphenol for use as component (i) is (−)-epigallocatechin gallate.

It has been found that very low amounts of the polyphenol content of component (i) are required to provide the desired malodour counteracting effect. Thus, the polyphenol content of component (i) is preferably from 0.05 to 1.5%, more preferably 0.1 to 1.0%, most preferably 0.2 to 0.8% by weight, based on the total weight of the malodour counteracting composition.

Typically, the concentration of the polyphenol content of component (i) in the oral care product used is from 10 to 20000 ppm, more preferably from 50 to 10000 ppm, even more preferably 75 to 2000 ppm, for example 100 to 1500 ppm. The desired effect cannot be obtained when the concentration of the polyphenol is lower than 10 ppm, while the suitability to taste becomes inferior caused by giving sour taste and bitterness when the concentration is higher than 20000 ppm.

Preferably component (i) is in the form of a solid, more preferably a powdered solid.

Base

The composition of the invention comprises, as component (ii), a base.

The present inventors have found that the effectiveness of the polyphenol at reducing the incidence of malodour due to thiols is dramatically improved if the polyphenol/thiol reaction occurs at a basic pH. However, since the composition is typically for use in the oral cavity which is usually slightly acidic, the presence of a base is found to be essential to achieve the desired pH.

Any suitable base can be used as long as it provides the desired elevated pH and is acceptable for use in an oral care product. For instance, preferred bases include baking soda, calcium lactate, calcium carbonate and calcium phosphate. Baking soda is particularly preferred.

To provide a highly effective malodour reduction, the pH within the oral cavity should be kept above neutral but must not be excessively high.

It has been found that below about pH 7.1 or above pH 9.0, the malodour counteracting ability of component (i) is significantly reduced. Therefore, the base is preferably present in an amount suitable to buffer the pH within the oral cavity to about 7.1 to 9.0, more preferably 7.4 to 8.6, most preferably 7.8 to 8.5, e.g. 8.1 to 8.4. Component (ii) is preferably present in an amount from 65 to 98%, more preferably from 70% to 97%, most preferably from 80 to 96.9% by weight based on the total weight of the malodour counteracting composition.

Preferably component (ii) is in the form of a solid.

Whilst the combination of component (i) with component (ii) has been found to provide a synergistic effect for counteracting thiol-based malodour, it has been found that storage of these components in contact with each other may actually inhibit the malodour counteracting effect.

Furthermore, it has also been found that chewing gum products, for instance, which are typically a uniform white colour, suffer from undesirable discoloration during storage when component (i) is not kept separate from component (ii). This is particularly apparent when component (ii) is a green tea extract.

For this reason, it is essential that component (i) is not in direct contact with component (ii) during storage of the composition and during storage of the oral care product comprising the composition.

Enzyme

Optionally and advantageously, the composition further comprises, as component (iii), an enzyme. The enzyme has been found to provide a synergistic effect with component (i) in counteracting malodour due to thiols.

A preferred class of enzymes are those obtained from natural edible plants or other food sources. A particularly preferred class of enzymes are polyphenol oxidases or polyphenol peroxidases.

For instance, enzymes found in mushroom and eggplant have been found to be particularly suitable for use as component (iii). Mushroom enzymes are the most preferred.

The polyphenol oxidase or peroxidase may be used in any suitable form known to the person skilled in the art. For instance, it can be extracted and then used as is. Suitable methods for extraction are well known in the art and do not require further explanation here.

The present inventors have found that the enzyme is particularly effective when it is present in acetone powder. Acetone powder is the residue obtained from homogenized raw food/plant material that has been washed with cold acetone.

In order for the composition to deliver excellent malodour counteracting benefits at very low doses in the oral cavity, it is advantageous if the weight ratio of powder containing the enzyme to polyphenol-containing extract is optimised. Excellent results are achieved within the preferred ratio range of from 2:1 to 200:1, more preferably from to 6:1 to 150:1, most preferably from 8:1 to 30:1.

Component (iii), when present in the form of acetone powder, is preferably present in an amount of from 1.4% to 9.5%, more preferably from 4.2% to 9.1%, most preferably from 5 to 8.8% by weight based on the total weight of the malodour counteracting composition.

Whilst the use of component (i) together with component (iii) has been found to provide a synergistic effect against thiol malodour, it has been found that storage of these components in contact with each other may inhibit this effect.

For this reason, it is essential that component (i) is not in direct contact with component (iii) during storage of the composition and during storage of the oral care product comprising the composition Encapsulation Component (i) is provided in an encapsulated form in the malodour-counteracting composition of the invention.

By encapsulated, it is meant that a barrier is provided around component (i) so that it is substantially not in direct contact with component (ii) or component (iii). This is beneficial for the reasons given above.

Furthermore, polyphenols are easily oxidised in the presence of air. Therefore, the barrier also preferably provides protection against oxidation of component (i) through exposure to the surrounding environment.

Component (ii) and/or component (iii) may also be individually encapsulated. This can be desirable since it provides a further barrier between component (i) and components (ii) and (iii).

The skilled person in the art is well aware of a variety of encapsulation systems which are suitable for this purpose, the following being preferred for their properties of providing very good barriers to oxidation.

A first preferred encapsulating system is a glassy matrix within which component (i) is held. More preferably the encapsulation system is a glassy carbohydrate matrix. The carbohydrate matrix ingredient preferably comprises a sugar derivative, more preferably maltodextrin.

Particularly preferred maltodextrins are those with a DE of from 10 to 30, more preferably from 15 to 25, most preferably from 17 to 19.

Typically, component (i) is admixed with a carbohydrate matrix material and an appropriate amount of a plasticizer, such as water, the mixture is heated within a screw extruder to a temperature above the glass transition temperature of the matrix material so as to form a molten mass capable of being extruded through a die and then the molten mass is extruded using established processes, such as described in the prior art. See, for instance, patent application WO 00/25606, published May 11, 2002 or WO 01/17372, published Mar. 15, 2001, and the documents cited therein, the contents of which are hereby included by reference.

If desired, further carbohydrate matrix components may be present to improve yet further the antioxidant barrier properties.

Other suitable encapsulation systems are described in, for examples, U.S. Pat. No. 4,610,890 or U.S. Pat. No. 4,707,367, the contents of which are included by reference.

The combined weight of the capsule and component (i) is preferably within the range of from 0.5 to 24.5%, more preferably 1 to 8%, most preferably 2 to 7% by weight, based on the total weight of the malodour controlling composition.

Other Optional Ingredients

The malodour counteracting composition may comprise other ingredients, such as those which improve the taste or flavour of the composition. Examples include mint oil, menthol and chlorophyll.

End Products

The malodour counteracting composition is for use in an oral care product. The oral care product is typically a solid or pasty substance since these provide a more stable environment for the malodour counteracting composition than liquid products. Preferred products include chewing gums or chewable functional sweets, toothpastes or toothbrushing powders and mouth rinse powder premixes.

The malodour counteracting composition will typically be present in an amount of from 1 to 15% by weight, based on the total weight of the oral care product, more preferably 2 to 12 wt %, most preferably 2.5 to 8 wt %.

Typically the malodour controlling composition is incorporated into the oral care product. Alternatively, it can be stored separately from the oral care product and mixed therewith when the oral care product is to be used.

For instance, it is well known to provide a toothpaste tube having first and second compartments and first and second outlets respectively. The outlets are arranged side by side so that, when the tube is squeezed, a single product is dispensed. Thus, a standard toothpaste composition may be held in one compartment whilst the malodour controlling composition is located in the other compartment.

EXAMPLES

The invention is now described with reference to the following examples.

The following compositions were prepared for use in the examples.

A methanethiol stock solution (A) was prepared by releasing 15.61 mg of methanethiol (ex Aldrich) from a sealed capillary tube into a 100 ml volumetric flask filled with cold 50% w/w aqueous PG solution, to give a concentration of 156.1 ppm methanethiol.

A buffer stock solution (B) for maintaining the correct alkaline pH during testing was prepared by weighing calculated amounts of $Na_2HPO_4.7H_2O$ (FW=268.1) and $NaH_2PO_4.H_2O$ (FW=137.99) into 100 mL volumetric flasks, the flasks then being filled to the mark with deionised water. The resulting solutions comprised 0.1 M phosphate buffers at desired pHs. A 0.1 M NaOH solution was used to adjust the pH as necessary.

Buffered stock Green Tea Extract samples (C) were prepared freshly by incorporating powdered green tea extract (Deodorising K, ex Taiyo Kagaku KK) into the buffer stock solution (B) at concentrations of 10 mg/mL.

For the control stock solution (D), degassed phosphate buffer solution (10 g) having a pH of 5.8 was weighed into a 20 mL glass vial (MicroLiter Analytical Supplier, Inc., metal seal LO, 20 mm with Tan PTFE/White Sil). The headspace was flushed with nitrogen before sealing with a crimp cap possessing a silicon septum with PTFE liner.

Methanethiol stock solution (A, 30 uL) was introduced into all the sample vials using a syringe and the final concentrations of methanethiol solutions were about 235 ppb.

Enzyme (E) was prepared in the form of acetone powder using the procedure described in the article O. Negishi, Y. Negishi and T. Ozawa, 2002, J. Agric. Food Chem., 50, 3856-3861. 100 g of raw white mushroom or eggplant (aubergine) were homogenized with 400 ml acetone at −10° C. in a Waring (tradename) blender. The products were filtered using coffee filter paper and the vegetable residues remaining on the paper were further washed by homogenising using cold aqueous 80% acetone solution. The residual acetone in the vegetable residues was then removed by rotary evaporation. The vegetable residues (acetone powders) were then lyophilized and stored at −10° C.

Example 1

Preparation of an Encapsulated Polyphenol

An encapsulated green tea extract was prepared by admixing the following ingredients in the amounts shown.

TABLE 1

| Ingredients | Grams | Wt % (dry) |
|---|---|---|
| 18 DE maltodextrin syrup [1] | 4459 | 81.50 |
| Green Tea Extract powder [2] | 630 | 16.00 |

TABLE 1-continued

| Ingredients | Grams | Wt % (dry) |
|---|---|---|
| Soya lecithin [3] | 39 | 1.00 |
| Agar agar [4] | 59 | 1.50 |
| Water | 400 | — |

[1] Glucidex ® C 1872, 72% solids; origin: Roquette America, Inc., Keokuk, Iowa, USA
[2] Deodorizing K, ex Taiyo Kagaku KK
[3] origin: Central Soya, Fort Wayne, Indiana, USA
[4] origin: TIC Gums Inc., Belcamp, Maryland, USA The agar was mixed with 400 g of water to form a slurry. This was added to the maltodextrin syrup. The mixture was heated to 123° C. to reduce the moisture content of the syrup. The green tea extract powder was mixed with the concentrated syrup and then extruded under $2 \times 10^5$ Pa pressure through a die plate with 0.8 mm diameter holes into a cold solvent for chilling and breaking of the strands. After drying, 0.5% silicon dioxide was added as free flow agent.

This encapsulated green tea extract is then suitable for use in any malodour counteracting composition.

Example 2

Effect of pH on the Capacity of Polyphenol to Reduce Thiol Concentration

A small amount of buffered stock green tea extract C (1 g) was weighed into a 20 mL glass vial and degassed phosphate buffer solution at the desired pHs shown in the table below was added to 10 g. The vial was sealed with a crimp cap. A small portion of methanethiol stock solution A (30 uL) was introduced using a syringe and the final concentration of methanethiol solution was about 325 ppb. Samples were incubated at 37° C. for 5 min before analyzed by GC-MS. Duplicate analysis was conducted for each sample. The methanethiol remaining was calculated by dividing the peak area of methanethiol from each sample by the peak area of methanethiol from the control stock solution D at each pH.

The results are given in the following table.

TABLE 2

| pH of sample | % of methanethiol remaining |
|---|---|
| Control | 100 |
| 5.72 | 101.8 |
| 7.31 | 51.1 |
| 7.50 | 34.8 |
| 7.70 | 22.4 |
| 7.79 | 16.4 |
| 8.0 | 8.0 |
| 8.18 | 5.7 |

At the same time, the level of dimethyl disulfide was tested and was found to remain substantially unchanged. This indicates that the lower level of methanethiol is due to removal by the green tea extract, rather than oxidation to dimethyl disulfide. The results also demonstrate the need for a pH above 7 in order to achieve significant reduction of the thiol.

Example 3

Effect of Varying the Amount of Green Tea Extract at pH 7.4 and 8.0

Example 2 was repeated at pH 7.4 and 8.0 and at the different levels of green tea. The results are given in the following table.

TABLE 3

| Amount of green tea extract (mg/ml) | % methanethiol remaining at pH 7.4 | % methanethiol remaining at pH 8.0 |
|---|---|---|
| Control | 100 | 100 |
| 0.1 | 67 | 28 |
| 0.5 | 46 | 11 |
| 1.0 | 58 | 7.8 |
| 1.5 | — | 7.8 |

The results demonstrate that an excellent effect is achieved at surprisingly low doses as long as the pH is sufficiently elevated.

Example 4

Effect of Presence of Enzyme

The effect of green tea extract at different pHs on the effectiveness of methanethiol reduction in the presence of acetone powder was evaluated.

A small amount of buffered green tea extract C (1.0 g) was weighed into a 20 mL glass vial which contained 20 mg of eggplant or mushroom acetone powder and degassed phosphate buffer solution (pH 5.0 or 7.4) was added to 10 g. The vial was sealed with a crimp top. A small portion of methanethiol stock solution A (30 uL) was introduced using a syringe and the final concentration of methanethiol solution was about 325 ppb. Samples were incubated at 37° C. for 5 min before analysis by GC-MS. Triplicate analyses were conducted for each sample. The methanethiol remaining was calculated by dividing the peak area of methanethiol from each sample by the peak area of methanethiol from the control D at each pH.

Following the method above but omitting ingredients as necessary, samples comprising (i) the green tea extract alone and (ii) the acetone powders alone were also prepared at pH 7.4

The results are given in the following table.

TABLE 4

| Composition | % methanethiol remaining at pH 5.0 | % methanethiol remaining at pH 7.4 |
|---|---|---|
| Control | 100 | 100 |
| Green tea extract | 88 | 59 |
| Eggplant acetone powder | — | 72 |
| Green tea extract + eggplant | 81 | 5.6 |
| Mushroom acetone powder | — | 40 |
| Green tea extract + mushroom | 43 | 2.7 |

The results demonstrate that at pH 7.4, dramatic improvements in thiol reduction are achieved when the green tea extract is used in the presence of small amounts of the acetone powders, compared with the results from green tea extract or enzyme alone.

Example 5

Further Evaluation of Varying Ingredient Levels at pH 7.4

The effects of the amount of green tea extracts and mushroom acetone powder on the percent remaining methanethiol in the headspace above an aqueous methanethiol solution at pH 7.4-7.5 were tested.

The samples were prepared according to the method set out in example 4, except that the green tea extract and acetone powder levels were varied as shown in the table below. The results are given in the following table. The maximum effectiveness (greater than 90% thiol reduction) was achieved when acetone powder was greater than 15 mg in the presence of a small amount of green tea extract at pH 7.4.

TABLE 5

| Green Tea Extract (mg/mL), total 10 mL | Mushroom Acetone Powder (mg) | % CH$_3$SH Remaining |
|---|---|---|
| 0 | 0 | 100 |
| 0.1 | 0 | 66 |
| 0.25 | 0 | 63 |
| 1.0 | 0 | 59 |
| 0 | 5 | 79 |
| 0.1 | 5 | 21 |
| 0.5 | 5 | 20 |
| 1.0 | 5 | 20 |
| 0 | 10 | 56 |
| 0.1 | 10 | 14 |
| 0.25 | 10 | 10 |
| 0.5 | 10 | 11 |
| 1.2 | 10 | 11 |
| 0 | 15 | 42 |
| 0.1 | 15 | 3.8 |
| 0.25 | 15 | 2.9 |
| 0.6 | 15 | 7.8 |
| 0 | 20 | 40 |
| 0.1 | 20 | 0.75 |
| 0.25 | 20 | 2.8 |
| 0.6 | 20 | 4 |
| 1.0 | 20 | 2.7 |

Example 6

Effect of Oxidation on Polyphenols at pH 7.4

Green tea extract (1 mg/mL, pH 7.4) was pre-oxidised by mixing the tea extract with mushroom acetone powder (20 mg) and leaving to stand at 37° C. for 2 hours. After filtration to remove the enzyme, 10 mL filtrate were transferred to a sealed vial and a small portion of methanethiol stock solution A (30 uL) was introduced using a syringe. Samples were incubated at 37° C. for 5 min before analysis by GC-MS. The methanethiol remaining was calculated by dividing the peak area of methanethiol from each sample by the peak area of methanethiol from the control at each pH. Green tea extract which was preoxidised by air was obtained by slowly bubbling air through the tea extract in buffer solution (1 mg/mL, pH 7.4) for 3 hours.

The results are given in the table below.

TABLE 6

| Composition | Days stored after pre-oxidation | % methanethiol remaining |
|---|---|---|
| Tea fresh | 0 | 59 |
| Tea pre-oxidized with enzyme | 0 | 76 |
| Tea pre-oxidized with air | 6 days | 95 |
| Tea pre-oxidized with air | 4 day | 100 |
| Tea pre-oxidized with air | 1 day | 84 |

Pre-oxidized tea extract is less effective than fresh green tea extract (59% remaining) under the same conditions. This demonstrated the need for the encapsulation of polyphenols.

Example 7

Effect of Varying pH on H$_2$S Concentration

Control samples were prepared as follows. Phosphate buffer solutions (10 g) at different pH values were weighed into 20 mL glass vials (MicroLiter Analytical Supplier, Inc., metal seal LO, 20 mm with Tan PTFE/White Sil). Each vial was sealed with a crimp cap possessing a silicon septum with a PTFE liner. One mL of 5% H$_2$S was introduced using a 2.5 mL gas tight syringe. The control was equilibrated in a 37° C. water bath for 5 min. Different volumes of 0.5 N hydrochloric acid were then injected into the vials to adjust the pH to about 6.

1) Samples with Green Tea Extract

Small amount of buffered stock green tea extract C (1 g) was added into a 20 mL glass vial and phosphate buffer solution B was added to 10 g. The vial was sealed with a crimp top. One mL of 5% H$_2$S was introduced using a 2.5 mL gas tight syringe. The sample was equilibrated in a 37° C. water bath for 5 min and then different volumes of 0.5 N hydrochloric acid were injected into the vials to adjust the pH to about 6.

2) Samples with Green Tea Extract and Acetone Powder:

The preparation of this sample was identical to that of the green tea extract except that, in a first step, acetone powder (20 mg) was weighed into the 20 mL glass vial.

The headspace of samples was analyzed by GC-MS. The H$_2$S remaining was calculated by dividing the peak area of H$_2$S from each sample by the peak area of H$_2$S from the control at each pH.

The results are given in the following table.

TABLE 7

| pH | Green tea extract (% H$_2$S remaining) | Green tea extract + enzyme (% H$_2$S remaining) |
|---|---|---|
| 5.80 | 96 | 72 |
| 6.37 | 92 | 60 |
| 7.20 | 82 | 40 |
| 7.54 | 58 | 27 |
| 7.83 | 55 | 16 |
| 8.01 | 31 | 0 |
| 8.10 | 17 | 0 |
| 8.22 | 13 | 0 |
| 8.30 | 14 | 0 |
| 8.41 | 19 | 0 |
| 8.70 | 22 | 5 |
| 10.0 | 41 | 14 |
| 11.0 | 52 | 12 |

Example 8

Chewing Gum Comprising the Malodour Counteracting Composition

A chewing gum was prepared having the following formulation.

TABLE 8

| Ingredient | Amount (wt %) |
|---|---|
| Mallorca ® gum[1] | 67.2 |
| Sorbitol | 5.6 |
| Syloid ® 244[2] | 10.2 |

TABLE 8-continued

| Ingredient | Amount (wt %) |
| --- | --- |
| Magnesium stearate | 2.0 |
| Encapsulated green tea extract[3] | 10.0 |
| Baking soda | 5.0 |

[1] origin: Cafosa, Spain
[2] origin: W. R. Grace Company; Davison Chemical Division.
[3] see example 1

The sorbitol and Syloid® 244 were premixed. The gum was sheared using a sigma-blade mixer until a temperature of 50-55° C. was reached. The premixed powder was added and mixed with the gum base raw material until a homogeneous system was obtained in the form of a stringy paste, after approximately 5 min. The agglomerated mix was removed from the sigma-blade mixer and left to cool to room temperature. Once the equilibrium was reached, the coarse particles were milled in a hammer mill and the resulting powder was sieved through a 1 mm sieve. The powder was then dry blended with the remaining ingredients. The blend thus obtained was compressed by means of a manual press (Specac® machine) under a compression force of between 1 and 4 tons. Tablets of 20 mm diameter were obtained.

The invention claimed is:

1. A composition for counteracting malodour due to thiols, the composition comprising:
   (i) a polyphenol, a source of polyphenol, a composition comprising polyphenol or mixtures thereof,
   (ii) a base present in an amount which elevates the pH to between about 7.4 and about 8.6, and optionally,
   (iii) an enzyme that provides a synergistic effect against thiol malodour when used together with component (i),
   wherein the polyphenol is separately encapsulated from the base and enzyme to substantially prevent direct contact with the base or enzyme, wherein the component (ii) base is separately encapsulated to further prevent contact with the component (i) polyphenol.

2. The composition according to claim 1, wherein component (i) is a polyphenol having the formula:

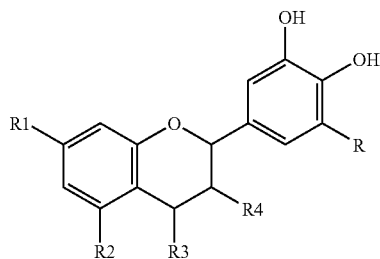

wherein
R, R1 and R2 are independently selected from H or —OH,
R3 is H, —OH or =O, and
R4 is —OH or

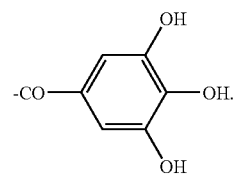

3. The composition according to claim 1, wherein component (i) is present in the form of a green tea extract.

4. The composition according to claim 1, wherein the polyphenol content of component (i) is from 0.05 to 1.5% by weight based on the total weight the composition.

5. The composition according to claim 1, wherein component (ii) is present in an amount from 65 to 98% by weight, based on the total weight of the composition.

6. The composition according to claim 1, wherein the component (iii) enzyme is present and is a polyphenol oxidase or polyphenol peroxidase.

7. The composition according to claim 1, wherein the component (iii) enzyme is present and is present in the form of an acetone powder.

8. The composition according to claim 7, wherein component (iii) is present in an amount of from 1.4% to 9.5% by weight, based on the total weight of the malodour counteracting composition.

9. A chewing gum comprising a composition as claimed in claim 1.

10. A toothpaste or toothpowder comprising a composition as claimed in claim 1.

11. A mouth rinse powder premix comprising a composition as claimed in claim 1.

12. A method of using a composition as claimed in claim 1, in an oral care product to reduce malodour due to thiols.

13. A composition for counteracting malodour due to thiols, the composition comprising:
   (i) a polyphenol, a source of polyphenol, a composition comprising polyphenol or mixtures thereof;
   (ii) a base present in an amount that elevates the pH; and
   (iii) an enzyme that provides a synergistic effect against thiol malodour when used together with the component (i) polyphenol,
   wherein the polyphenol is separately encapsulated from other components to substantially prevent direct contact with the base or enzyme, wherein the component (ii) base and/or component (iii) enzyme is separately encapsulated from the other components so that the base does not substantially contact components (i) and (iii).

14. The composition of claim 13, wherein the polyphenol is separately encapsulated in a glassy matrix that provides a barrier to oxidation.

15. The composition of claim 13, wherein the component (iii) enzyme is present in the form of an acetone powder.

16. The composition of claim 13, wherein the component (ii) base is present in a sufficient amount to elevate the pH to between about a pH of 7.4 and about a pH of 8.6.

* * * * *